(12) United States Patent
Neuhann

(10) Patent No.: US 6,413,277 B1
(45) Date of Patent: Jul. 2, 2002

(54) METHOD FOR INTRAOCULAR LENS INSERTION AND APPARATUS

(76) Inventor: Tobias H. Neuhann, Clemensstrasse 94, Munich (DE), 80331

(*) Notice: Subject to any disclaimer, the term of this patent is extended or adjusted under 35 U.S.C. 154(b) by 0 days.

(21) Appl. No.: 09/574,151

(22) Filed: May 18, 2000

(51) Int. Cl.$^7$ .................................................. A61F 2/16
(52) U.S. Cl. ..................... 623/6.39; 623/6.11; 623/6.38; 623/6.41; 623/6.43
(58) Field of Search ............................... 623/5.12, 6.11, 623/6.14, 6.38, 6.39, 6.4, 6.41, 6.42, 6.43, 6.44, 6.45, 6.51

(56) References Cited

U.S. PATENT DOCUMENTS

| | | | |
|---|---|---|---|
| 4,113,088 A | * | 9/1978 | Blinkhorst .................. 206/210 |
| 4,280,232 A | * | 7/1981 | Hummel ........................ 623/6 |
| 4,446,581 A | * | 5/1984 | Blake ............................. 623/6 |
| 4,542,540 A | | 9/1985 | White |
| 4,726,367 A | * | 2/1988 | Shoemaker .................. 128/303 |
| 5,047,051 A | * | 9/1991 | Cumming ....................... 623/6 |
| 5,766,244 A | | 6/1998 | Binder |
| 5,824,074 A | | 10/1998 | Koch |
| 5,843,184 A | | 12/1998 | Clonni |
| 5,919,230 A | | 7/1999 | Sambursky |
| 2001/0004708 A1 | * | 6/2001 | Nagai .......................... 623/4.1 |

FOREIGN PATENT DOCUMENTS

| | | |
|---|---|---|
| EP | 0884030 | 12/1998 |
| EP | 0 884 031 | 12/1998 |
| EP | 0968727 | 1/2000 |

* cited by examiner

Primary Examiner—Paul B. Prebilic
Assistant Examiner—Will H Matthews
(74) Attorney, Agent, or Firm—Sam Silverberg

(57) ABSTRACT

An improved method of inserting an intraocular lens into an eye comprising removing an existing lens so as to leave a capsular bag intact; at least partially inserting an intraocular lens having at least one haptic incorporating an aperture therein into the capsular bag; and inserting a capsular tension ring into the capsular bag such that the capsular tension ring passes through the aperture is disclosed. A replacement lens arrangement and a sterile packaging therefore are also disclosed.

14 Claims, 4 Drawing Sheets

METHOD FOR INTRAOCULAR LENS INSERTION AND APPARATUS

FIELD OF THE INVENTION

The present invention relates generally to a methods for the insertion of an intraocular lens into an eye. More specifically, the invention is directed to the insertion of a lens into the capsular bag after the natural lens has been removed, for example because of the presence of a cataract. The invention also relates to the resulting arrangement and a packaging for use therein.

BACKGROUND OF THE INVENTION

The insertion of artificial lenses into patients is a process familiar to ophthalmic surgeons. Cataract removal may be intracapsular or extracapsular. Intracapsular cataract extraction includes complete removal of the lens, the capsular bag enveloping the lens, and the zonules connecting the capsular bag to the scleral wall of the eye. Extracapsular cataract extraction is performed to remove the cataractous lens while leaving the capsular bag and zonules intact within the posterior chamber of the eye. In this procedure, a capsulorhexis incision is performed to remove a generally circular mid-portion of the anterior capsule of the capsular bag, thereby leaving the posterior capsule, an annular anterior capsular flap and a generally circular anterior capsulorhexis edge. The cataractous lens is removed from the residual capsular bag and replaced with an artificial IOL. The IOL has haptics to engage an inner peripheral surface of the residual capsular bag and centralize the IOL within the capsular bag. The present invention is related to replacement lens insertion following extracapsular lens removal.

IOLs may be subdivided into two types. A first type is referred to by the term plate haptic lens, described for example in U.S. Pat. No. 5,919,230 incorporated herein by reference for all purposes. These plate haptic lenses may be hard and non-foldable or soft and foldable. Soft lenses are preferred because they may be inserted through a smaller incision.

A second type of IOL is referred to by the term "J" or "C" haptic foldable lenses which have two or more generally J- or C-shaped legs extending from a central lens, described for example in U.S. Pat. No. 4,542,540 and PCT Application No. PCT/JP98/05370 (WO99/27978 and European Patent Application EP 0 968 727 A1) both incorporated herein by reference for all purposes.

A known problem of soft plate haptic lenses in particular is their tendency, once implanted, to be affected by capsular shrinkage. Because the materials used are relatively soft they do not resist such a shrinkage of the capsular bag. Plate haptic lenses can also suffer from decentration accompanied by capsular shrinkage and spontaneous luxation after YAG laser treatment.

There is a desire to be able to replace the natural lens with a lens which provides a correction of astigmatism. Such a lens is available from the Staar Surgical Company, Monrovia, Calif. in the form of a toric foldable plate haptic lens. Because of the astigmatism correction, it is particularly important that such lenses do not rotate after insertion. In order to reduce the occurrence of lens rotation, the manufacturers provide fenstrations in the haptics to allow fibrous lens epithelial cells to grow through and provide a securing mechanism.

Another IOL which is designed to correct for astigmatism is described in U.S. Pat. No. 5,824,074 and comprises two IOLs which can be rotated with respect to each other to provide the necessary correction. This design has a particular requirement for preventing subsequent rotation of the lenses.

Solutions for preventing the rotation of inserted IOLs have been proposed. As indicated above, the plate haptic IOLs from the Staar Surgical Co. include fenestrations to promote fixation through the growth of cells. Other concepts include suturing, as described in European Patent Application EP 0 884 030 A2, in which a "C" haptic foldable lens incorporates loops on the locating legs which are attached by a transscleral suture. A disadvantage with the former solution is that a certain period of time is required for the cells to grow through the fenestration and secure the lens and a disadvantage of the latter is that the suturing is a further invasive procedure.

There exists a need for improved methods and materials for the insertion of an intraocular lens.

SUMMARY OF THE INVENTION

It is an object of the present invention to provide a means for securely locating an intraocular lens in position. The present invention provides a method for inserting an intraocular lens into an eye comprising the steps of removing an existing lens so as to leave a capsular bag intact; at least partially inserting an intraocular lens having at least one haptic incorporating an aperture therein into the capsular bag; and inserting a capsular tension ring into the capsular bag such that the capsular tension ring passes through the aperture.

Preferably, the lens to be inserted is a toric lens which may correct for astigmatism in the treated eye. Such a toric lens may be a plate haptic lens or otherwise. The capsular tension ring may be adapted to self-locate itself relative to the intraocular lens by means of a loop in its shape.

The invention further provides an intraocular lens arrangement comprising an optical lens having at least one haptic attached thereto, the haptic having an aperture therein and a capsular tension ring threaded through the aperture.

In a still further aspect of the invention, there is provided a sterile package of items comprising a replacement intraocular lens having at least one haptic, the at least one haptic having an aperture therein; and a capsular tension ring.

The methods and apparatus described herein may generally be used in animals, preferably in mammals such as humans, cats, and dogs, and more preferably in humans.

A further understanding of the nature and advantages of the inventions herein may be realized by reference to the following description of embodiments of the invention with reference to the attached drawings.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
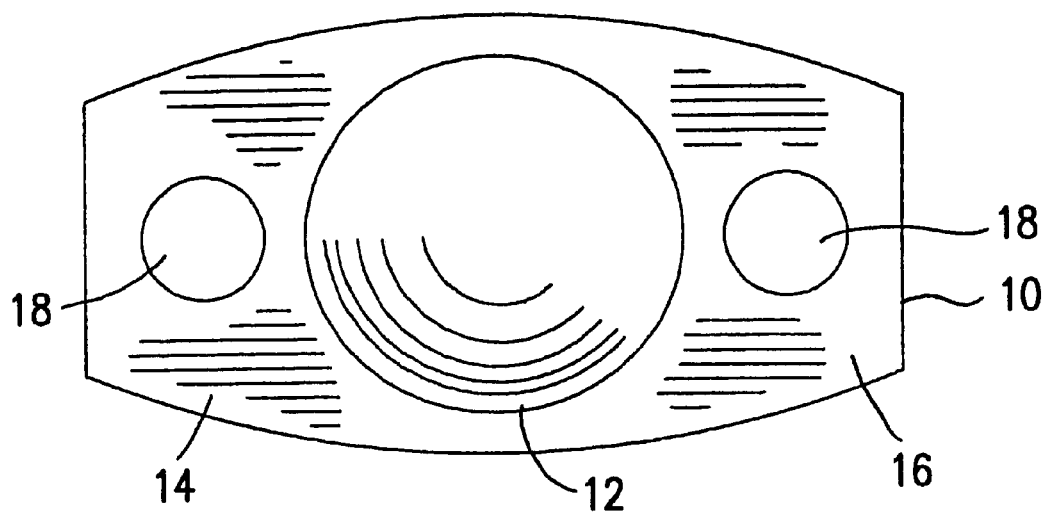
FIG. 1 shows a plate haptic lens.

Referring to FIG. 1, there is shown a foldable plate haptic IOL 10. The IOL lens has a central optical region 12 and two plate haptics 14 and 16. Preferably the IOL 10 is a toric lens available from the Staar Surgical Company of Monrovia, Calif. having the product code AA-4203TF. This plate haptic lens is manufactured from silicone and has a fenestration 18 in each of the haptics 14 and 16.

Figure 2:
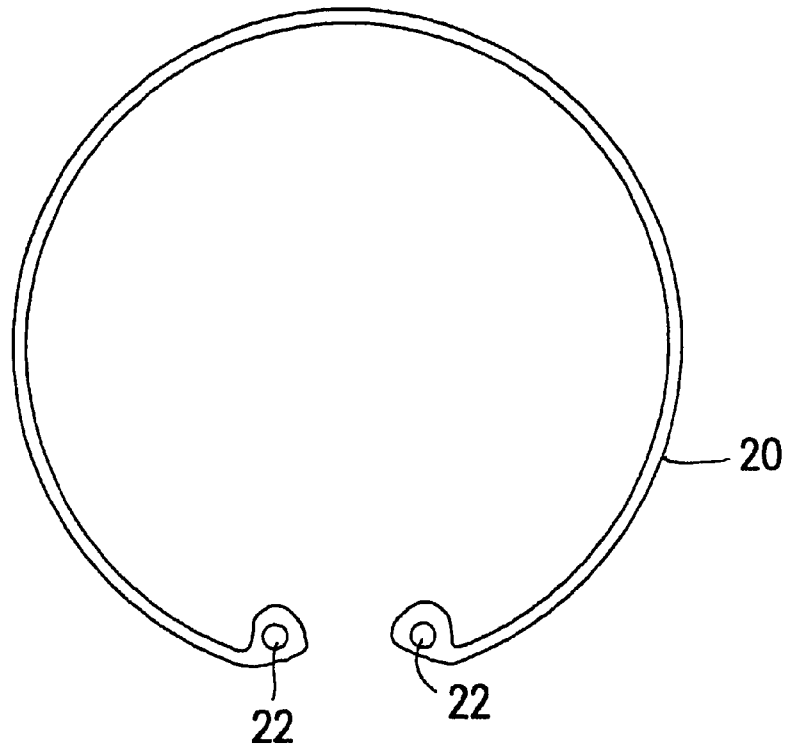
FIG. 2 shows a capsular tension ring.

Referring to FIG. 2, there is shown a capsular tension ring 20 in the form of an open loop with an eye 22 at each end of the loop. Preferably the capsular tension ring is of a type available from Morcher GmbH of Stuttgart Germany identified as a "Type 14" tension ring. Such tension rings are described in European Patent Application EP 0 884 031.

Referring now to FIGS. 3A–F, there are shown the steps involved in inserting the lens 10 and the capsular tension ring 20 into the capsular bag 24 of a patient's eye. Prior to the insertion of the lens 10, the natural lens, or an earlier implanted IOL, has been removed leaving an anterior rim 26 of the capsular bag 24. Known techniques for such lens removal include ultrasonic emulsification techniques well known to a skilled surgeon and need not be described here.

Figure 3A:
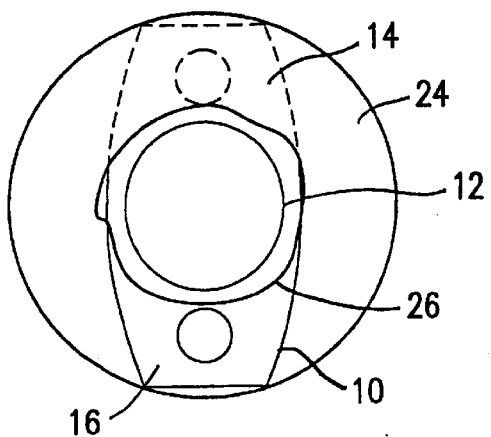
FIGS. 3A–F show steps performed in inserting the FIG. 1 lens and the FIG. 2 capsular tension ring.
Figure 3B:
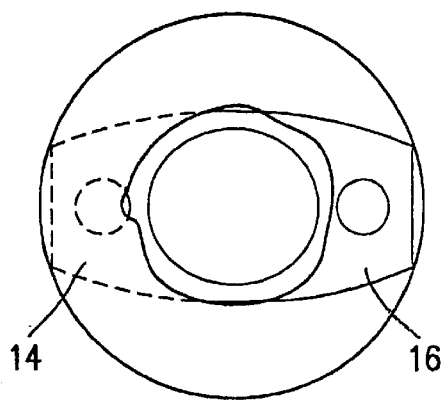

Prior to insertion, the lens 10 is folded along its long axis and held in a known system for injection into the eye. In a first step, shown in FIG. 3A, the lens 10 is implanted with the distal plate haptic 14 being inserted into the capsular bag. The proximal haptic 16 is not yet positioned inside the capsular bag. The lens is then rotated by approximately 90° using a manipulator (not shown) acting on the fenestration 18 of the exposed haptic 16. This rotation is shown in FIG. 3B.

Figure 3C:
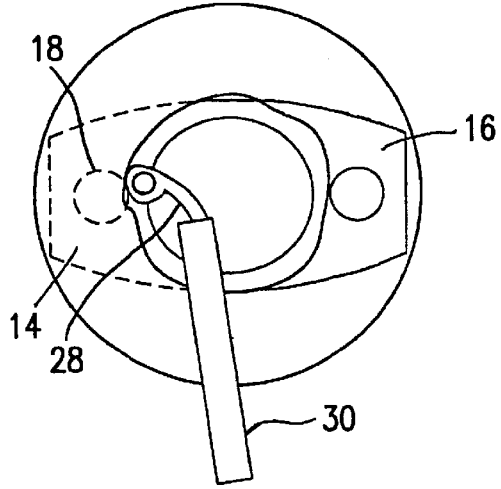

The next stage which is performed is the introduction of the capsular tension ring 20. This is introduced such that it passes through the fenestration of the haptic 14 which is within the capsular bag. As shown in FIG. 3C, a first end 28 of the tension ring 20 is pushed out of an injector 30. As a result of the 90° rotation of the lens 10 from its initial position, the fenestration 18 of the plate haptic 14 is ideally placed for the end 28 to pass through it.

Figure 3D:
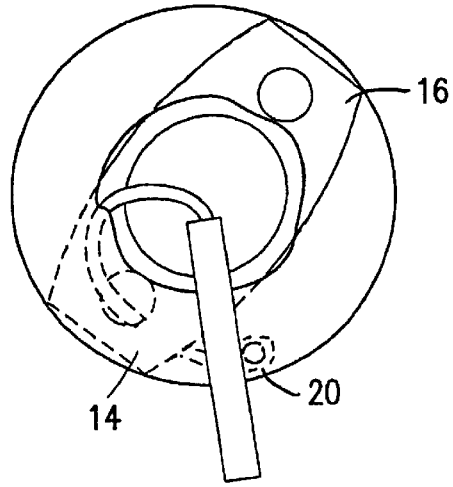
Figure 3E:
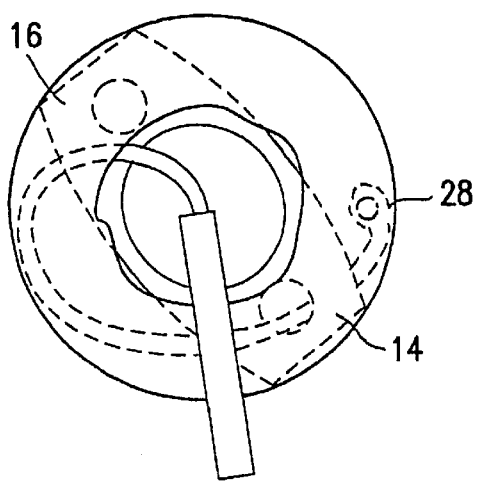
Figure 3F:
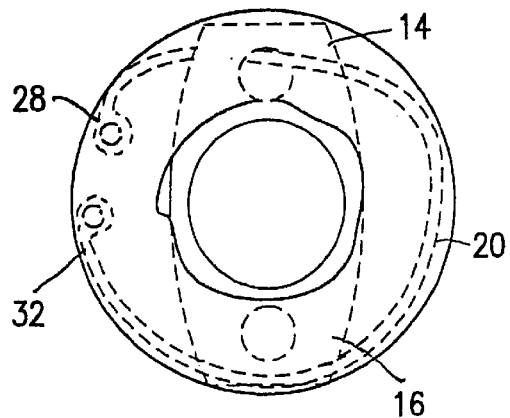

The tension ring 20 is further pushed out of the injector 30. This causes the lens 10 to rotate in the capsular bag, as shown in FIG. 3D. As a result, the haptic 16 slips beneath the anterior capsular rim as shown in FIG. 3E. Finally, the second end 32 of the tension ring 20 is released to become located in the capsular equator, as shown in FIG. 3F. If necessary, the inserted lens can be rotated through further use of a manipulator such as a dialing hook (not shown).

Preferably, the replacement lens together with the capsular tension ring are supplied in a single sterilized package for the use of a surgeon.

The combination of a plate haptic lens and a capsular tension ring threaded through one of the plate haptics of the lens provides a lens implant which reduces the effect of capsular shrinkage and decentration. Experiments have shown that external pressure on the sclera does not affect the intraocular lens position. Furthermore, YAG laser capsulotomies could be performed without any problems. None of the three known major problems of silicon plate haptic lenses occurred, namely capsular phimosis syndrome, primary and secondary IOL decentration and IOL luxation after posterior capsulotomy.

If necessary, the IOL can be exchanged after implantation. In this procedure, the lens is first divided into two pieces, one of which has the capsular tension ring threaded through the fenestration. The plate with the ring is maneuvered so that an injector can hook the ring and aspirate it. The residual IOL is then removed.

Whilst the invention has been described with reference to plate haptic lenses, the principles of the invention can be applied to other types of IOL. For example, it may be possible to combine a "C" haptic lens with a capsular tension ring. For this solution at least one of the haptics should have a suitable eyelet through which ring can be threaded. European Patent Application No. EP 0 884 030 A2 is referred to in this regard. A toric "C" haptic lens could thus be envisaged, with the capsular tension ring providing the necessary locating mechanism.

It has been observed that where the capsular tension ring threads through the fenestration of the plate haptic, there is a tendency, once inserted in the eye, for the tension ring to be displaced slightly from the capsular equator. Also, the plate haptic may be caused to twist about its plane.

Figure 4:
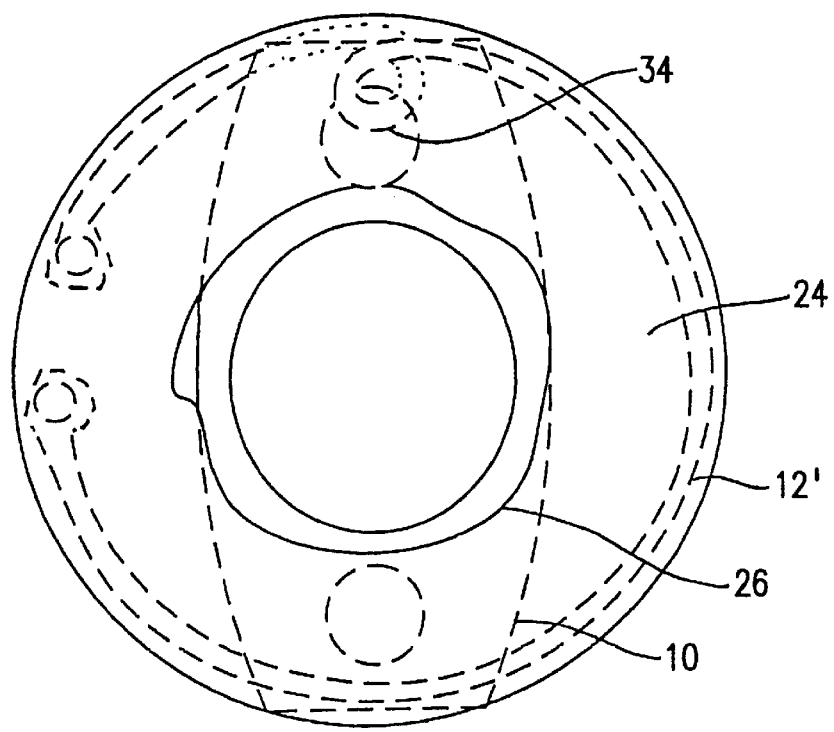
FIG. 4 shows a combination of a plate haptic lens and a looped capsular tension ring.
Figure 5:
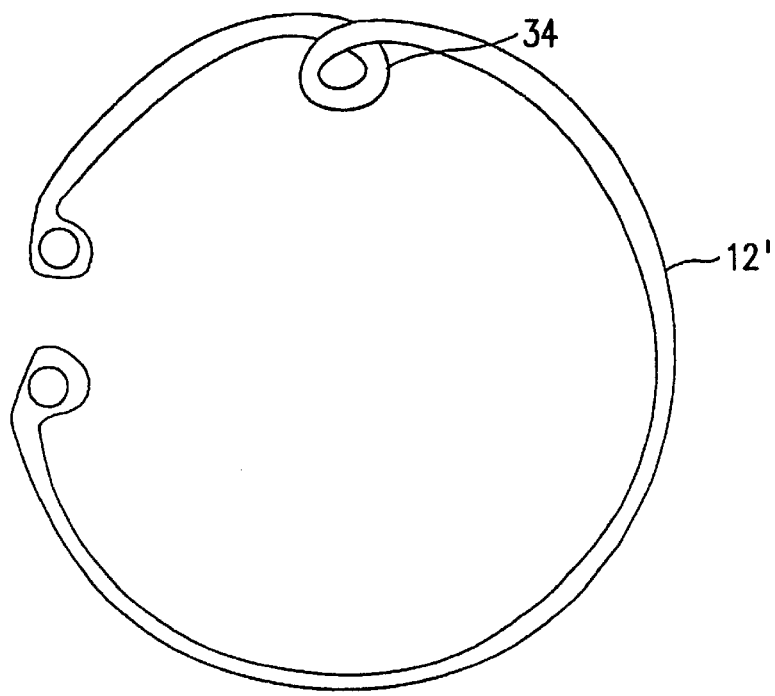
FIG. 5 shows the looped capsular tension ring of FIG. 4.

Referring to FIGS. 4 and 5, a possible improvement would consist of the use of a capsular tension ring 12' which is not uniformly curved but includes a loop 34. This loop 34 would be located at the plate haptic fenestration as shown in FIG. 4. The advantage of such a solution is that the plane of the plate haptic is not affected by the presence of the tension ring and stays flat.

Figure 6A:
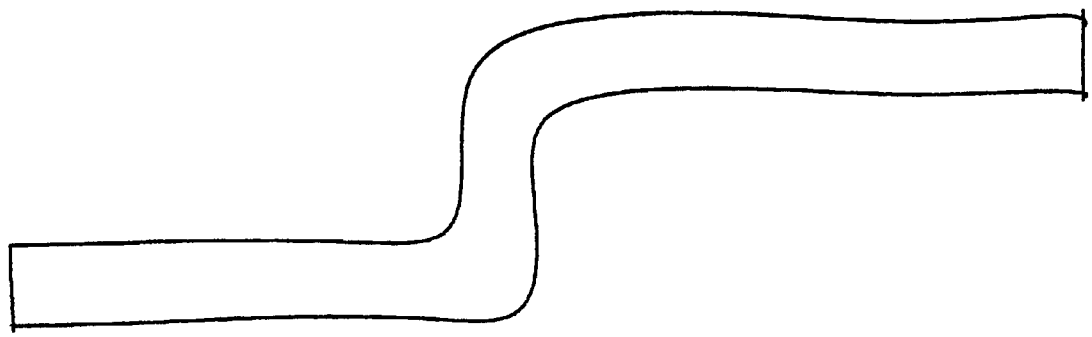
FIGS. 6A–B show possible modifications to the capsular tension ring.
Figure 6B:
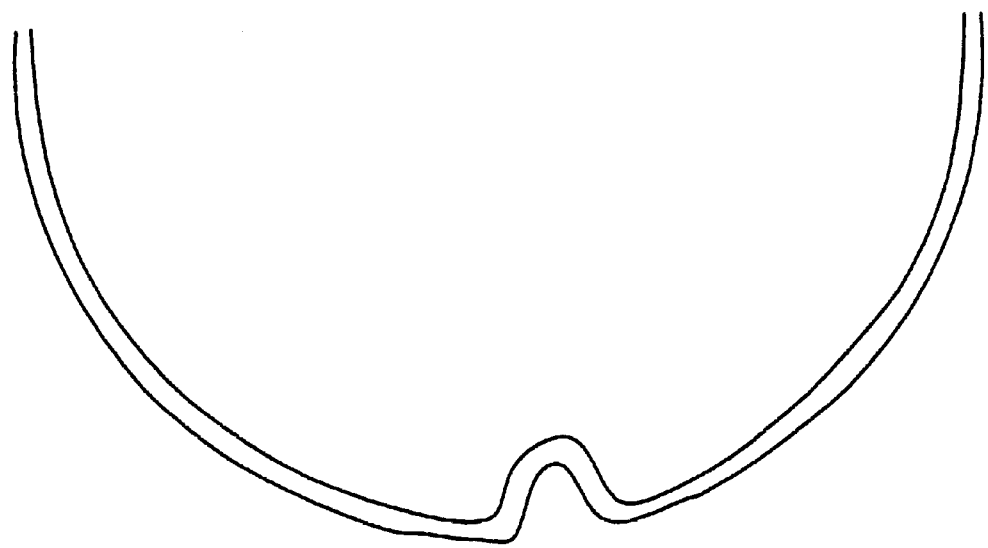

Instead of the loop 34, the tension ring 12 could have a change in level of the two halves of the tension ring in the form of a step between the two levels as shown in FIG. 6A, this being a side view of the tension ring. Rather than a step, a more gentle slope transition could be employed. Such a change in level could be combined with a kink in the curved shape of the tension ring as shown in plan view in FIG. 6B. Such a kink would help to keep the tension ring in the equatorial position in the capsular bag. Of course, the kink of FIG. 6B could be employed without a change in level at all.

A further possible modification would be the use of plate haptic lenses having a loop or fenestration closer to the outer periphery of the haptic. U.S. Pat. No. 5,047,051, incorporated herein by reference for all purposes, shows a plate haptic lens having loop members at the outer edges of the haptics which could receive a capsular tension ring.

Although preferred embodiments have been described in detail herein, it will be apparent to the expert in the relevant art that various modifications and substitutions and the like can be made within the spirit of the invention and these modifications and substitutions can be considered to be within the scope of the invention in accordance with the following claims.

What is claimed is:

1. A method for inserting an intraocular lens into an eye comprising the steps of:
   removing an existing lens so as to leave a capsular bag intact;
   at least partially inserting an intraocular lens having at least one haptic incorporating an aperture therein into the capsular bag;
   and after the at least partial insertion, inserting a unitary capsular tension ring having two free ends into the capsular bag wherein one free end is threaded through said aperture and the free ends are not secured to the haptic.

2. The method of claim 1, wherein the intraocular lens is a plate haptic lens.

3. The method of claim 1, wherein the intraocular lens is a toric lens.

4. An intraocular lens arrangement comprising:
   an optical lens having at least one haptic attached thereto, said haptic having an aperture therein; and a unitary capsular tension ring, having two free ends, and wherein one end has been threaded through said aperture such that the body of said capsular tension ring remains within said aperture and the free ends are not secured to the haptic.

5. The arrangement of claim 4, wherein the at least one haptic is a plate haptic.

6. The arrangement of claim 4, wherein the optical lens is toric.

7. The arrangement of claim 4, wherein the capsular tension ring incorporates a loop therein.

8. The method of claim 1 wherein the other free end is located in the capsular equator.

9. The arrangement of claim 4 wherein one end of said capsular tension ring passes through said aperture and wherein the other end is located in the capsular equator.

10. The arrangement of claim 7 wherein said loop is located at the aperture.

11. An intraocular lens arrangement comprising:
   an optical lens having at least one haptic attached thereto, said haptic having an aperture therein; and a unitary capsular tension ring, having two free ends, and wherein one end has been threaded through said aperture such that the body of said capsular tension ring remains within said aperture and the free ends are not secured to the haptic wherein the tension ring is not uniformly curved.

12. The arrangement of claim 11 wherein the not uniformly curved tension ring includes a loop.

13. The arrangement of claim 11 wherein the not uniformly curved tension ring includes a step creating a change in level within the ring.

14. The arrangement of claim 11 wherein the not uniformly curved tension ring includes a kink.

* * * * *